(12) United States Patent　　　　(10) Patent No.:　US 12,678,528 B2

Zhao　　　　　　　　　　　　　　　　(45) Date of Patent:　Jul. 14, 2026

(54) AROMATHERAPY APPARATUS

(71) Applicant: Chongqing Tianyu E-Commerce Co., Ltd., Chongqing (CN)

(72) Inventor: Caitian Zhao, Chongqing (CN)

( * ) Notice: Subject to any disclaimer, the term of this patent is extended or adjusted under 35 U.S.C. 154(b) by 461 days.

(21) Appl. No.: 18/532,045

(22) Filed: Dec. 7, 2023

(65) Prior Publication Data

US 2024/0189474 A1　　Jun. 13, 2024

(30) Foreign Application Priority Data

Dec. 12, 2022　(CN) .......................... 202223324825.8

(51) Int. Cl.
A61L 9/12　　　　　(2006.01)
(52) U.S. Cl.
CPC ...................................... A61L 9/12 (2013.01)
(58) Field of Classification Search
CPC ....................................................... A61L 9/12
See application file for complete search history.

(56)　　　　　References Cited

U.S. PATENT DOCUMENTS

2010/0294849 A1 * 11/2010 Groner ................... A61H 33/02
　　　　　　　　　　　　　　　　　　　　　　422/306
2021/0213471 A1 * 7/2021 Richard ................... A61L 9/03

* cited by examiner

*Primary Examiner* — Sean E Conley

(57)　　　　　　　ABSTRACT

Disclosed is an aromatherapy apparatus. The aromatherapy apparatus structure includes an outer housing, a driving inner housing, an aromatherapy bracket, and a top cover. The outer housing is a housing of which one end is opened, an inner wall of the outer housing is provided with a longitudinal limiting groove, the driving inner housing is arranged inside the outer housing, an upper end of the driving inner housing is provided with a rotating portion, the rotating portion is located at an opening of the outer housing, a side wall of the driving inner housing is provided with a spiral clamping groove, the aromatherapy bracket is arranged inside the driving inner housing, a bottom portion of the aromatherapy bracket is provided with a clamping column, and the top cover is connected to a top position of the aromatherapy bracket. The aromatherapy apparatus is simple in structure, convenient in operation.

10 Claims, 3 Drawing Sheets

AROMATHERAPY APPARATUS

CROSS-REFERENCE TO RELATED APPLICATIONS

This application claims priority to Chinese Patent Application No. 202223324825.8, filed on Dec. 12, 2022, which is incorporated herein by reference in its entirety.

TECHNICAL FIELD

The present application relates to the technical field of aromatherapies, in particular to an aromatherapy apparatus.

BACKGROUND

With the improvement of the quality of daily life, people's pursuit is also higher and higher. When the people are in a space for a long time, they may feel tired and be unable to concentrate. In order to solve this problem, some items that may emit an odor, such as an aromatherapy apparatus, are usually used. The aromatherapy apparatus in the space may keep the air clean, remove unpleasant odors in the air, kill bacteria, and play a role of purifying the air. A fresh and pleasant atmosphere is created in the space, so that the people in the space may feel happy.

Chinese patent CN214316799U discloses a portable mosquito repelling apparatus, including an outer housing, a driving inner housing, and a mosquito repellent liquid placement assembly. The outer housing is a housing of which one end is opened, the driving inner housing is arranged inside the outer housing, the driving inner housing is provided with a rotating button, the rotating button is rotatably arranged on the opening end of the outer housing, the mosquito repellent liquid placement assembly is arranged inside the driving inner housing, an inner wall of the outer housing is provided with a spiral groove, the driving inner housing is provided with a longitudinal channel, both ends of the longitudinal channel on the driving inner housing are provided with horizontal limiting channels that are opposite to each other, and the mosquito repellent liquid placement assembly includes a bottom seat, a placement cavity, an emitting column, and a top cover. This structure is convenient for opening the apparatus at any time, may be used repeatedly, and is not limited by locations, thus the usage rate of the portable mosquito repelling apparatus is improved. However, its pipe structure is complex, and there are many usage steps.

How to simplify the structure of the aromatherapy apparatus and make its usage operations more convenient becomes a problem that those skilled in the art need to solve.

SUMMARY

The present application aims to solve technical problems in existing technologies, and a purpose is to provide an aromatherapy apparatus with simple structure and convenient operations.

The purpose of the present application is achieved by the following technical schemes, and it is specifically as follows.

An aromatherapy apparatus, characterized by including: an outer housing, a driving inner housing, an aromatherapy bracket, and a top cover, the outer housing is a housing of which one end is opened, an inner wall of the outer housing is provided with a longitudinal limiting groove, the driving inner housing is arranged inside the outer housing, an upper end of the driving inner housing is provided with a rotating portion, the rotating portion is located at an opening of the outer housing, a side wall of the driving inner housing is provided with a spiral clamping groove, the aromatherapy bracket is arranged inside the driving inner housing, a bottom portion of the aromatherapy bracket is provided with a clamping column, and the top cover is arranged at a top end of the aromatherapy bracket.

Further preferably, the aromatherapy bracket is provided with two clamping columns, and the inner wall of the outer housing is provided with two longitudinal limiting grooves.

Furthermore preferably, the two clamping columns are symmetrically arranged on both sides of the bottom portion of the aromatherapy bracket, and the two longitudinal limiting grooves are symmetrically arranged on both sides of the inner wall of the outer housing.

Further preferably, a positioning column is arranged in a middle position of the bottom portion of the outer housing, and a column groove is correspondingly arranged in a middle position of the driving inner housing and the aromatherapy bracket.

Furthermore preferably, the positioning column is a conical positioning column.

Further preferably, the top cover is connected with the aromatherapy bracket by a clamping button.

Further, a bottom end of the spiral clamping groove is provided with a connecting section, and the connecting section extends downwards and is communicated with a bottom end of the driving inner housing.

Further, a top end of the aromatherapy bracket is provided with a clamping groove, and a bottom end of the top cover is provided with a clamping portion cooperated with the clamping groove.

Further, a top portion of the inner wall of the outer housing is provided with an annular groove, an outer side of a top portion of the driving inner housing is provided with an annular protrusion, and the annular protrusion is cooperated with the annular groove.

Since the above technical schemes are adopted, the beneficial effects produced are as follows: by the rotating portion rotatably arranged at the upper end of the driving inner housing, the driving inner housing is rotated relative to the outer housing. Since the bottom portion of the aromatherapy bracket is provided with the clamping column, and the driving inner housing is correspondingly provided with the spiral clamping groove, when the driving inner housing is rotated, the spiral clamping groove and the above clamping column arranged at the bottom of the aromatherapy bracket may cause the aromatherapy bracket arranged inside the driving inner housing to move upwards, and a perfume in the aromatherapy bracket is diffused into the air to emit an odor. The aromatherapy apparatus is simple in structure, and convenient in operation.

DETAILED DESCRIPTION OF THE EMBODIMENTS

Figure 1:
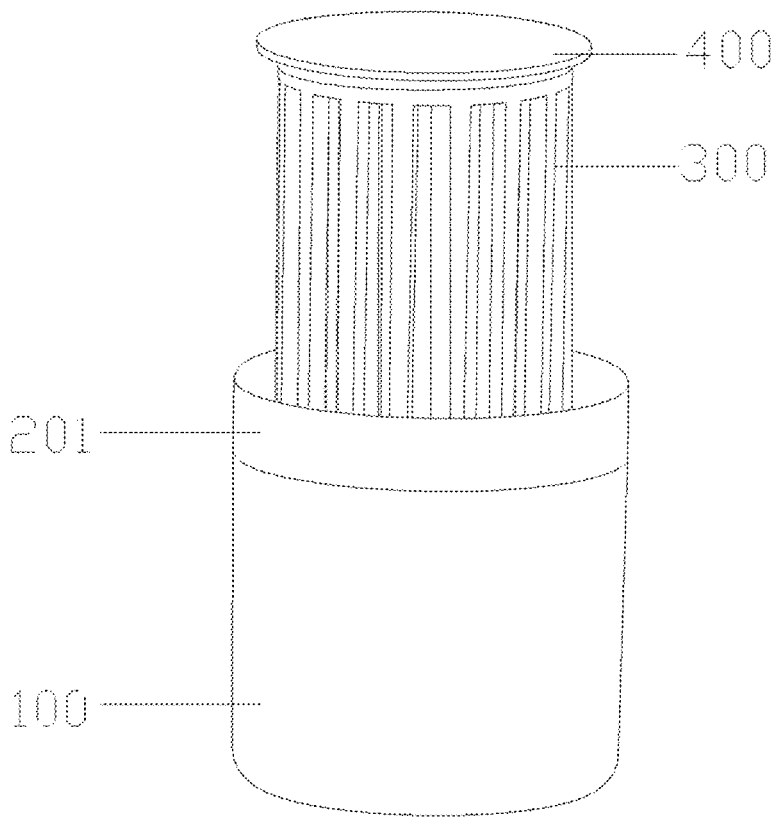
FIG. 1 is a structure schematic diagram of an aromatherapy apparatus of the present application.

In the description of the present application, it should be understood that the orientation or position relationship indicated by terms "longitudinal", "transverse", "up", "down", "front", "back", "left", "right", "vertical", "horizontal", "top", "bottom", "inside", "outside" and the like is an orientation or position relationship based on drawings, and only for the convenience of describing the present application and simplifying the description, rather than indicating or implying that an apparatus or element referred to must have a specific orientation, or be constructed and operated in the specific orientation, therefore it may not be understood as limitations to the present application.

In the description of the present application, unless otherwise specified and limited, it should be noted that terms "installation", "connection", and "linkage" should be understood in a broad sense. For example, it may be mechanical or electrical connection, or internal communication between two elements, or direct connection, or indirect connection by an intermediate medium. For those of ordinary skill in the art, the specific meanings of the above terms may be understood according to specific circumstances.

In the description of this description, the description of reference terms such as "one embodiment", "some embodiments", "example", "specific example", or "some examples" means that specific features, structures, materials, or characteristics described in combination with the embodiment or example are contained in at least one embodiment or example of the present application. In this description, schematic expressions of the above terms do not necessarily refer to the same embodiments or examples. Moreover, the specific features, structures, materials, or characteristics described may be combined in an appropriate manner in any one or more embodiments or examples.

The embodiments of the present application are described in detail below, and examples of the embodiments are shown in the drawings, herein the same or similar mark numbers throughout represent the same or similar elements or elements with the same or similar functions. The embodiments described below with reference to the drawings are exemplary and are only intended to explain the present application and may not be understood as limitations to the present application.

As shown in FIGS. 1 to 4, the present application discloses an aromatherapy apparatus, and its structure includes an outer housing 100, a driving inner housing 200, an aromatherapy bracket 300, and a top cover 400. The outer housing 100 is a housing of which one end is opened, an inner wall of the outer housing 100 is provided with a longitudinal limiting groove 101, the driving inner housing 200 is arranged inside the outer housing 100, an upper end of the driving inner housing 200 is provided with a rotating portion 201, the rotating portion 201 is located at an opening of the outer housing 100, a side wall of the driving inner housing 200 is provided with a spiral clamping groove 202, the aromatherapy bracket 300 is arranged inside the driving inner housing 200, a bottom portion of the aromatherapy bracket 300 is provided with a clamping column 301, the clamping column 301 extends into the longitudinal limiting groove 101 after passing through the spiral clamping groove, and the top cover 400 is arranged at a top end of the aromatherapy bracket 300.

Figure 2:
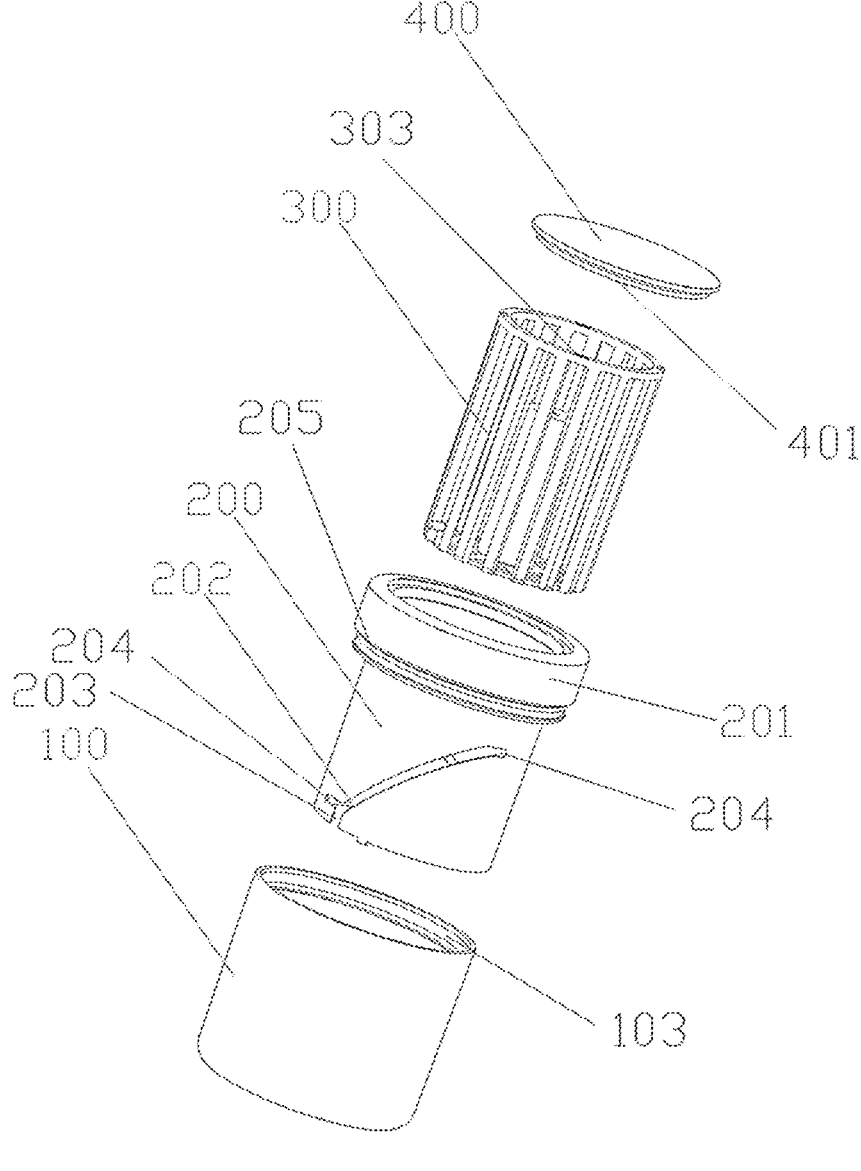
FIG. 2 is an exploded view of the present application.
Figure 3:
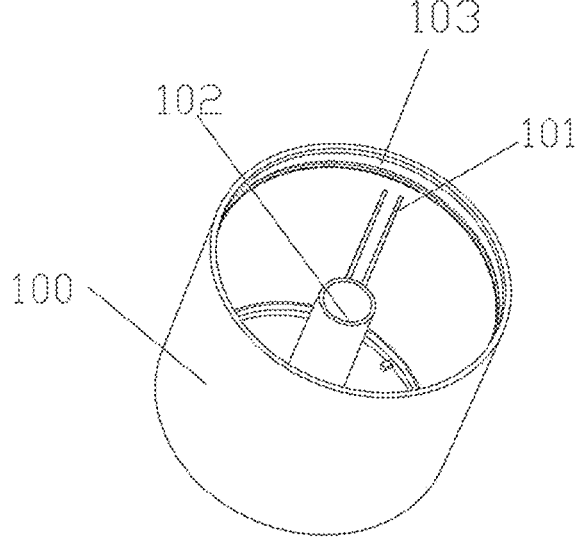
FIG. 3 is a structure schematic diagram of an outer housing of the present application.
Figure 4:
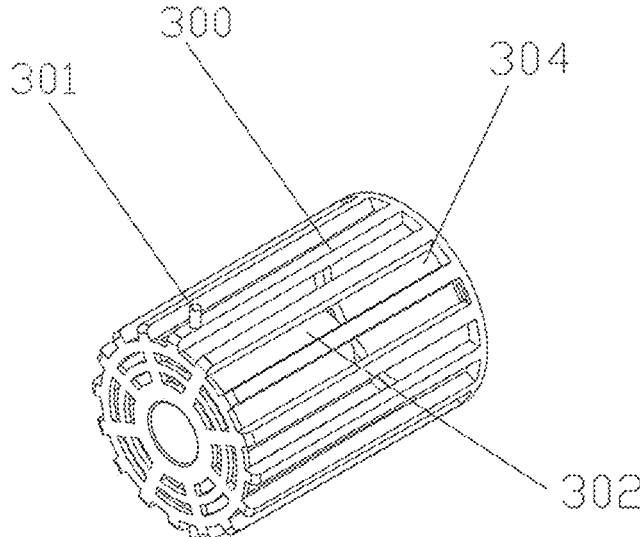
FIG. 4 is a structure schematic diagram of an aromatherapy bracket of the present application.

As shown in FIGS. 1 and 2, the aromatherapy apparatus includes the outer housing 100, herein the outer housing 100 is a housing of which one end is provided with an opening, the inner wall of the outer housing 100 is provided with the longitudinal limiting groove 101, the longitudinal limiting groove 101 is composed of two rectangular strips, and a top portion of the inner wall of the outer housing 100 is provided with an annular groove 103.

The driving inner housing 200 is arranged inside the outer housing 100, and the upper end of the driving inner housing 200 is provided with the rotating portion 201. When the driving inner housing 200 is arranged inside the outer housing 100, the above rotating portion 201 is located at the opening end of the outer housing 100, namely the rotating portion 201 at its upper end is exposed to the air outside the outer housing 100. The side wall of the driving inner housing 200 is provided with the spiral clamping groove 202, an outer side of a top portion of the driving inner housing 200 is provided with an annular protrusion 205, the annular protrusion 205 is cooperated with the annular groove 103 mutually, the annular protrusion 205 and the annular groove 103 are used to prevent the driving inner housing 200 from detaching from the outer housing 100, and the rotation of the driving inner housing 200 is not affected.

The interior of the driving inner housing 200 is provided with the aromatherapy bracket 300, a top end of the aromatherapy bracket 300 is opened, and the aromatherapy bracket 300 is arranged inside the driving inner housing. In addition, the middle position of the aromatherapy bracket 300 is a hollow pipeline support structure, the surface of the aromatherapy bracket 300 is provided with a plurality of strip-shaped holes 304, the bottom portion of the aromatherapy bracket 300 is provided with the clamping column 301, the clamping column 301 extends into the longitudinal limiting groove 101 after passing through the spiral clamping groove 202, a perfume that emits an odor is placed in the aromatherapy bracket 300, and the top cover 400 is detachably arranged at the top end of the aromatherapy bracket 300.

When the outer housing 100, the driving inner housing 200, and the aromatherapy bracket 300 are assembled integrally, the aromatherapy bracket 300 is located inside the driving inner housing 200, and the driving inner housing 200 is located inside the outer housing 100 except for the rotating portion 201 at its top end. In addition, the above clamping column 301 arranged at the bottom portion of the aromatherapy bracket 300 corresponds to the spiral clamping groove 202 arranged on the side wall of the driving inner housing 200, and the clamping column 301 at the bottom portion of the aromatherapy bracket 300 extends out of the spiral clamping groove 202 of the driving inner housing 200, and extends to the longitudinal limiting groove 101 arranged on the inner side wall of the outer housing 100.

When the aromatherapy apparatus is used, it is only necessary to rotate the rotating portion 201 on the upper portion of the driving inner housing 200, so that the driving inner housing 200 is rotated relative to the outer housing 100. At this time, the clamping column 301 in the bottom position of the aromatherapy bracket 300 is located in the spiral clamping groove 202 arranged in the side wall position of the driving inner housing 200. Since the shape of the spiral clamping groove 202 is spiral and the longitudinal limiting groove 10 limits the clamping column 301 to move only upwards and downwards, when the driving inner housing 200 is rotated, it may push the clamping column 301 to move upwards, and simultaneously drive the aromatherapy bracket 300 to move upwards, so that the aromatherapy bracket 300 is ascended to the exterior of the driving inner housing 200 and exposed to the air, and the perfume located inside the aromatherapy bracket 300 emit the odor into the air. The clamping column 301 also extends into the longitudinal limiting groove 101 arranged on the side wall of the outer housing 100, and further limits the aromatherapy bracket 300 to move only upwards and downwards. Since the above aromatherapy apparatus is simple in structure, the operation of using the aromatherapy apparatus is also very convenient.

Further preferably, in other embodiments of the present application, optionally the bottom portion of the aroma- therapy bracket 300 is provided with two clamping columns 301, and the two clamping columns 301 are uniformly distributed and arranged on a bottom circumference of the aromatherapy bracket 300. Correspondingly, the side wall of the driving inner housing 200 is provided with two spiral clamping grooves 202, and the inner side wall of the outer housing 100 is provided with two longitudinal limiting grooves 101. The two clamping columns 301 are symmetri- cally arranged on the bottom portion of the aromatherapy bracket 300, so that the upward and downward displacement of the aromatherapy bracket 300 is more stable when the aromatherapy apparatus is used, thus the using stability of the aromatherapy apparatus is improved.

Further preferably, in other embodiments of the present application, optionally the middle position of the bottom portion of the outer housing 100 is provided with a posi- tioning column 102, and correspondingly, the middle posi- tion of the driving inner housing 200 and the aromatherapy bracket 300 is provided with a column groove 302 which is used to place the positioning column 102. After the posi- tioning column 102 is arranged, when the aromatherapy apparatus is mounted, it is another positioning apparatus. In addition, when the aromatherapy apparatus is used, the driving inner housing 200 is rotated by using the positioning column 102 as a center, to guarantee the movement stability of the driving inner housing 200, thereby the displacement stability of the aromatherapy bracket 300 is improved, and correspondingly the using stability of the aromatherapy apparatus is improved.

Further preferably, in other embodiments of the present application, the middle portion of the bottom end of the outer housing 100 is provided with the positioning column 102, the outer surface of the positioning column 102 has a certain slope, the positioning column 102 is vertically arranged, the positioning column 102 is coaxial with the outer housing 100, the driving inner housing 200, and the aromatherapy bracket 300, the positioning column 102 passes through the driving inner housing 200 and the aro- matherapy bracket 300 sequentially, the interior of the aromatherapy bracket 300 is provided with the column groove 302, the column groove 302 is wrapped on the outer side of the positioning column 102, and the positioning column 102 may be used for mounting and positioning of the outer housing 100, the driving inner housing 200, and the aromatherapy bracket 300, as well as rotational positioning. When the aromatherapy apparatus is used, the driving inner housing 200 is rotated by using the positioning column 102 as a rotating axis, and the aromatherapy bracket 300 is ascended and descended by using the positioning column 102 as a guide rod, thus the stability of the apparatus is improved.

Furthermore preferably, in other embodiments of the present application, optionally the positioning column 102 may be arranged as a hollow cylinder with a taper, the hollow cylinder with the taper not only facilitates de- molding in the production process and improves the manu- facturing efficiency of the aromatherapy apparatus; but also guarantees the higher using stability of the aromatherapy apparatus while materials of the aromatherapy apparatus are saved and costs are reduced.

Further preferably, in other embodiments of the present application, optionally the top cover 400 may be connected with the aromatherapy bracket 300 by a clamping button. A top end position of the aromatherapy bracket 300 is provided with a clamping groove 303, and a clamping portion 401 is correspondingly arranged around the top cover 400. When it is necessary to replace the perfume of the aromatherapy apparatus, the top cover 400 arranged at the top end of the aromatherapy bracket 300 needs to be opened for operating, and a perfume replacing operation is performed. When the top cover 400 is connected with the aromatherapy bracket 300 by the clamping button, operations of mounting and detaching the top cover 400 are very convenient, thus the convenience of using the aromatherapy apparatus is improved.

Further preferably, in other embodiments of the present application, as shown in FIG. 2, the bottom end of the spiral clamping groove 202 is provided with a connecting section 203, the connecting section 203 is communicated with a bottom surface of the driving inner housing 200, and the connecting section 202 is used to place the clamping column 301 into the spiral clamping groove 202, as to facilitate the assembly of the clamping column 301 and the spiral clamp- ing groove 202. The top end and the bottom end of the spiral clamping groove 202 are both provided with horizontal sections 204. When the rotating portion 201 is rotated so that the aromatherapy bracket 300 is ascended to a top limit position or enters the driving inner housing 200, the clamp- ing column 301 is located at the top end or bottom end of the spiral clamping groove 202 at this time. The rotating portion 201 may be further rotated so that the clamping column 301 is moved into the horizontal section 204 and the aroma- therapy bracket 300 is located in a locked state. In the case without an external force, the aromatherapy bracket 300 remains relatively stationary.

Although the embodiments of the present application are already shown and described, those of ordinary skill in the art may understand that: various changes, modifications, replacements, and variations may be made to these embodi- ments without departing from the principles and purposes of the present application, and the scope of the present appli- cation is limited by the claims and equivalents thereof.

What is claimed is:

1. An aromatherapy apparatus, comprising: an outer hous- ing, a driving inner housing, an aromatherapy bracket, and a top cover, wherein the outer housing is a housing of which one end is opened, an inner wall of the outer housing is provided with a longitudinal limiting groove, the driving inner housing is arranged inside the outer housing, an upper end of the driving inner housing is provided with a rotating por- tion, the rotating portion is located at an opening of the outer housing, a side wall of the driving inner housing is provided with a spiral clamping groove, the aroma- therapy bracket is arranged inside the driving inner housing, a bottom portion of the aromatherapy bracket is provided with a clamping column, and the top cover is arranged at a top end of the aromatherapy bracket.

2. The aromatherapy apparatus according to claim 1, wherein the aromatherapy bracket is provided with two clamping columns, and the inner wall of the outer housing is provided with two longitudinal limiting grooves.

3. The aromatherapy apparatus according to claim 2, wherein the two clamping columns are symmetrically arranged on both sides of the bottom portion of the aroma- therapy bracket, and the two longitudinal limiting grooves are symmetrically arranged on both sides of the inner wall of the outer housing.

4. The aromatherapy apparatus according to claim 1, wherein a positioning column is arranged in a middle position of the bottom portion of the outer housing, and a column groove is correspondingly arranged in a middle position of the driving inner housing and the aromatherapy bracket.

5. The aromatherapy apparatus according to claim 3, wherein the positioning column is a conical positioning column.

6. The aromatherapy apparatus according to claim 1, wherein the top cover is connected with the aromatherapy bracket by a clamping button.

7. The aromatherapy apparatus according to claim 3, wherein the top cover is connected with the aromatherapy bracket by a clamping button.

8. The aromatherapy apparatus according to claim 1, wherein a bottom end of the spiral clamping groove is provided with a connecting section, and the connecting section extends downwards and is communicated with a bottom end of the driving inner housing.

9. The aromatherapy apparatus according to claim 1, wherein a top end of the aromatherapy bracket is provided with a clamping groove, and a bottom end of the top cover is provided with a clamping portion cooperated with the clamping groove.

10. The aromatherapy apparatus according to claim 1, wherein a top portion of the inner wall of the outer housing is provided with an annular groove, an outer side of a top portion of the driving inner housing is provided with an annular protrusion, and the annular protrusion is cooperated with the annular groove.

\*    \*    \*    \*    \*